United States Patent [19]

Teach et al.

[11] Patent Number: 4,557,756
[45] Date of Patent: Dec. 10, 1985

[54] META-ANILIDE AND META-ANILIDE UREA HERBICIDAL COMPOUNDS AND METHODS OF USE

[75] Inventors: Eugene G. Teach, El Cerrito; Jeffery T. Springer, El Sobrante, both of Calif.

[73] Assignee: Stauffer Chemical Company, Westport, Conn.

[21] Appl. No.: 567,282

[22] Filed: Dec. 30, 1983

[51] Int. Cl.$^4$ .................. C07C 127/19; C07C 103/87
[52] U.S. Cl. ........................................ 71/118; 71/120; 564/153; 564/50; 260/453 RW
[58] Field of Search ................................ 564/153, 50; 260/453 RW; 71/118, 120

[56] References Cited

U.S. PATENT DOCUMENTS 4,056,524 11/1977 Walker .......................... 260/239 BF
4,137,070 1/1979 Pallos et al. ............................ 71/100
4,406,692 9/1983 Wong ..................................... 564/50

Primary Examiner—Charles F. Warren
Assistant Examiner—Carolyn S. Greason
Attorney, Agent, or Firm—Michael J. Bradley

[57] ABSTRACT

A compound having the structural formula

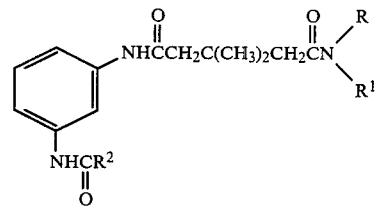

wherein
R is hydrogen or $C_1$-$C_3$ alkyl, preferably methyl;
$R^1$ is $C_1$-$C_3$ alkyl, preferably ethyl; and
$R^2$ is $C_1$-$C_3$ alkyl, preferably ethyl; $C_1$-$C_2$ alkylamino, preferably methylamino; $C_2$-$C_4$ dialkylamino, preferably dimethylamino; or $C_2$-$C_4$ alkylalkoxyamino, preferably methylmethoxyamino; and its use as a post-emergent herbicide.

13 Claims, No Drawings

META-ANILIDE AND META-ANILIDE UREA HERBICIDAL COMPOUNDS AND METHODS OF USE

BACKGROUND OF THE INVENTION

The present invention relates to certain meta-anilide and meta-anilide urea compounds which are useful as herbicides and particularly useful as post-emergent herbicides against annual and perennial grasses and broadleaf weeds.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

THE PRIOR ART

U.S. Pat. Nos. 3,642,891, 3,723,474 and 3,941,581 disclose related anilide ureas but fail to disclose the manufacture and use of anilide ureas having an amido group on the amide chain.

Efforts are constantly being made, however, to find compounds which are equal to or greater in effectiveness than presently existing compounds, or which are more economical to produce.

DESCRIPTION OF THE INVENTION

This invention relates to the production of novel meta-anilide and meta-anilide urea compounds and their use as post-emergent herbicides. The novel compounds of this invention have the following structural formula

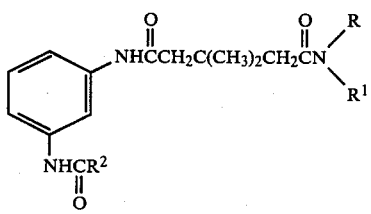

wherein
R is hydrogen or $C_1$–$C_3$ alkyl, preferably methyl;
$R^1$ is $C_1$–$C_3$ alkyl, preferably ethyl; and
$R^2$ is $C_1$–$C_3$ alkyl, preferably ethyl; $C_1$–$C_2$ alkylamino, preferably methylamino; or $C_2$–$C_4$ dialkylamino, preferably dimethylamino; or $C_2$–$C_4$ alkylalkoxyamino, preferably methylmethoxyamino.

In the above description of the compounds of this invention, alkyl includes both straight- and branched-chain configurations; for example, methyl, ethyl, n-propyl and isopropyl.

The compounds of the invention can be produced in a multi-step process in accordance with the following generalized sequence of steps. R, $R^1$ and $R^2$ are as defined above.

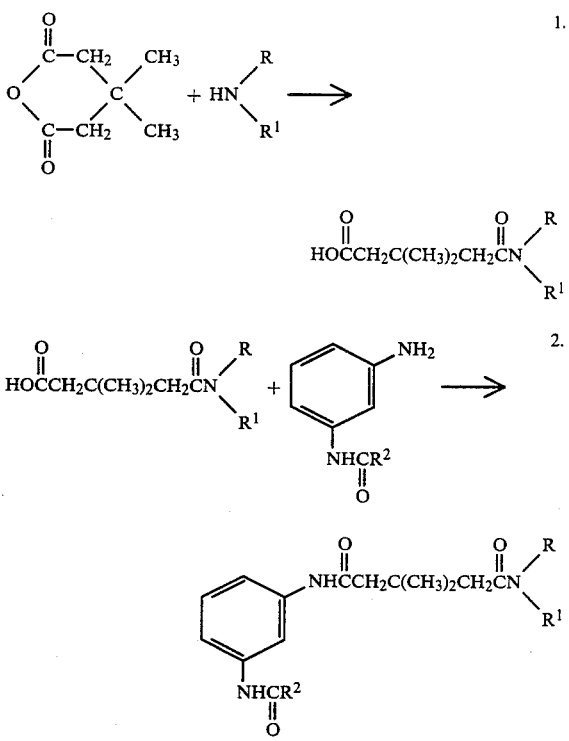

The compounds of this invention can be prepared using the following method:

A methylene chloride solution is prepared by adding an excess of the desired amine at about room temperature. The solution is cooled to about $-5°$ C. and the anhydride is added dropwise after being dissolved in methylene chloride. The cooling bath is removed and product work up is begun when the reaction solution reaches room temperature. The solution is washed and dried, followed by rotary evaporation. The isolated acid is then combined with an acid acceptor in tetrahydrofuran (or other dry solvent) at reduced temperature. The acylation reaction (step 2 above) to form the desired meta-anilide urea is conducted by adding a properly substituted anilide to the acid/solvent mixture in the presence of a catalytic amount of methane sulfonyl chloride at reduced temperature. Work up comprises rotary evaportion, extraction, water washings, drying with sodium sulfate, and rotary evaporation again.

The end product compounds can be produced by selecting any one of the compounds produced in accordance with steps 1 and 2 above and continuing the reaction sequence as indicated.

The example below illustrates making the compounds of the invention using various starting materials. All intermediates and final products were identified by infrared, nuclear magnetic resonance and proton magnetic resonance spectra.

EXAMPLE

Preparation of N′,N′-Dimethyl-3,3-Dimethyl-N-(M-Dimethylureido Phenyl)Glutaramide Step 1: Approximately 44 grams of dimethylamine was bubbled into 700 ml methylene chloride that was magnetically stirred at room temperature. The solution was cooled to −5° C. and 25 grams 3,3-Dimethyl glutaric anhydride dissolved in 75 ml methylene chloride was added. The cooling bath was then removed. When the reaction mixture reached room temperature, it was washed three times with water, dried with sodium sulfate, and rotary evaporated. The yield was 30.2 grams 1-(N,N-dimethylamido)3,3-dimethyl glutaramic acid.

Step 2: N,N-Dimethyl-3,3-dimethyl glutaramic acid (2.6 grams) and 1.5 gram triethyl amine were mixed in 150 ml tetrahydrofuran. The mixture was stirred magnetically and cooled to −5° C. Methane sulfonyl chloride (1.7 gram) was added dropwise and stirred at −5° C. for one hour. 1-(3-amino phenyl)-3,3-dimethyl urea (2.49 grams) was dissolved in 35 ml tetrahydrofuran. This solution was added dropwise and stirred for one hour at −5° C. The cooling bath was then removed. When the reaction mixture reached room temperature it was concentrated by rotary evaporation. Methylene chloride (175 ml) was added and the mixture washed once with 10 percent w/w NaOH, twice with water and dried over sodium sulfate. Rotary evaporation yields 1.1 grams of the title compound. This compound will be referred to as compound No. 3.

TABLE I

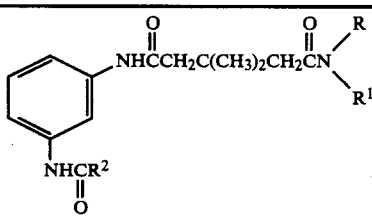

| Compound No. | R | R$^1$ | R$^2$ | $n_D^{30}$ or Melting Point |
|---|---|---|---|---|
| 1 | —CH$_3$ | —CH$_3$ | —NHCH$_3$ | 1.5358 |
| 2 | —CH$_3$ | —CH$_3$ | —CH$_2$CH$_3$ | 1.5559 |
| 3 | —CH$_3$ | —CH$_3$ | —N(CH$_3$)$_2$ | 1.5448 |
| 4 | —H | —CH$_3$ | —CH$_2$CH$_3$ | 1.5420 |
| 5 | —H | —CH$_3$ | —NHCH$_3$ | 60.0–67.0 |

HERBICIDAL SCREENING TESTS

As previously mentioned, the herein described compounds produced in the above-described manner are phytotoxic compounds which are useful and valuable in controlling various plant species. Selected compounds of this invention were tested as herbicides in the following manner.

Post-emergence herbicide test. Seven grass and broadleaf weed species, including green foxtail (FT) (*Setaria viridis*), watergrass (WG) (*Echinochloa crusgalli*), wild oat (WO) (*Avena fatua*), annual morningglory (AMG) (*Ipomoea purpurea*), velvetleaf (VL) (*Abutilon theophrasti*), mustard (MD) (*Brassica kaber*) and curly dock (CD) (*Rumex crispus*), are seeded in individual rows in 6×10×3 inch flats. The flats are placed in the greenhouse, watered daily (both before and after chemical treatment) with a sprinkler and maintain at about 78° F. Chemical spray tratment is made 12 days after planting. The spray is prepared by weighing out 333 mg of compound and dissolving in 25 ml acetone containing 1% polyoxyethylene sorbitan monolaurate emulsifier. From this stock solution 18 ml are removed and brought up to a 40 ml volume with a 19:1 water/acetone mixture. The carrier volume is 80 gallons/A (748 L/ha) and a 4 lb/A (4.48 kg/ha) rate is used.

Watering of the treated flats is confined to the soil surface and not to the foliage of the sprouted plants. Twelve-fourteen Days after treatment, the degree of injury or control is determined by comparison with untreated check plants of the same age. The injury rating from 0 to 100% is recorded for each species as percent control with 0% representing no injury and 100% representing complete control.

The results of the post-emergence herbicide test are reported in Table II.

TABLE II

| | Post-Emergence Herbicidal Activity Application Rate - 4.48 kg/ha | | | | | | | | |
|---|---|---|---|---|---|---|---|---|---|
| Cmpd. No. | FT | WG | WO | AMG | VL | MD | CD | AVE GR | AVE BL |
| 1 | 0 | 0 | 10 | 25 | 0 | 40 | 0 | 3 | 16 |
| 2 | 0 | 0 | 0 | 20 | 20 | 30 | 10 | 0 | 20 |
| 3 | 100 | 60 | 35 | 80 | 80 | 75 | 100 | 65 | 83 |
| 4 | 0 | 0 | 0 | 25 | 10 | 40 | 0 | 0 | 19 |
| 5 | 0 | 0 | 0 | 30 | 0 | 35 | 0 | 0 | 16 |

AVE GR = The average of all grass weeds treated at the application rate.
AVE BL = The average of all broadleaf weeds treated at the application rate.

The compounds of the present invention are useful as herbicides, especially as post-emergence herbicides, and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil as a dispersion in water or other liquid. These granules are dust-free and free flowing when dry and yet upon dilution in water, form homogeneous dispersions. Typical carriers for dry flowables include fuller's earth, kaolin clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifier concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

| EXAMPLES OF TYPICAL FORMULATIONS | | | |
| --- | --- | --- | --- |
| Ingredient | | | Weight % |
| Oil | | | |
| Compound 1 | | | 1 |
| Oil solvent-heavy aromatic naphtha | | | 99 |
| Total | | | 100 |
| Emulsifiable Concentrate | | | |
| Compound 2 | | | 50 |
| Kerosene | | | 45 |
| Emulsifying agent (mixture of long chain ethoxylated polyethers with long chain sulfonate) | | | 5 |
| Total | | | 100 |
| Compound 3 | | | 90 |
| Kerosene | | | 5 |
| Emulsifying agent (mixture of long chain ethoxylated polyethers with long chain sulfonate) | | | 5 |
| Total | | | 100 |
| Dusts and/or Powders | | | |
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers and other herbicides, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof, triazine derivatives, such as 2,4-bis(3-methoxypropylamino)-6-methylthio-s-triazine, 2-chloro-4-ethylamino-6-isopropylamino-s-triazine, and 2-ethylamino-4-isopropyl-amino-6-methyl-mercapto-s-triazine; urea derivatives, such as 3-(3,5-dichlorophenyl)-1,1-dimethylurea and 3-(p-chlorophenyl)-1,1-dimethylurea; and acetamides such as N,N-diallyl-α-chloroacetamide, and the like; benzoic acids such as 3-amino-2,5-dichlorobenzoic acid; thiocarbamates such as S-propyl N,N-dipropylthiocarbamate, S-ethyl N,N-dipropyl thiocarbamate, S-ethyl cyclohexylethylthiocarbamate, S-ethyl hexahydro-1H-azepine-1-carbothioate and the like; anilines such as 4-(methylsulfonyl)-2,6-dinitro-N,N-substituted aniline, 4-trifluoromethyl-2,6-dinitro-N,N-di-n-propyl aniline, 4-trifluoromethyl-2,6-dinitro-N-ethyl-N-butyl aniline, 2-[4-(2,4-dichlorophenoxy)phenoxy]propanoic acid, 2-[1-(ethoxyimino)-butyl]-5-[2-ethylthio)propyl]-3-hydroxy-2-cyclohexene-1-one, (±)-butyl-2[4-[(5-trifluoromethyl)-2-pyridinyl)oxy]phenoxy]propanate, sodium 5-[2-chloro-4-(trifluoromethyl)phenoxy]-2-nitrobenzoate, 3-isopropyl-1H-2,1,3benzothiadiazine-4(3H)-one-2,2-dioxide, and 4-amino-6-tert-butyl-3(methylthio)-as-triazin-5(4H)-one or (4-amino-6-(1,1-dimethylethyl)-3(methylthio)-1,2,4-triazin-5(4H)-one). Fertilizers useful in combination with the active ingredients include, for example, ammonium nitrate, urea and superphosphate. Other useful additaments include materials in which plant organisms take root and grow such as compost, manure, humus, sand, and the like.

We claim:

1. A compound having the structural formula

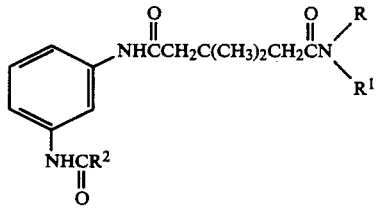

wherein R is selected from the group consisting of hydrogen or $C_1$–$C_3$ alkyl; $R^1$ is selected from the group consisting of $C_1$–$C_3$ alkyl; and $R^2$ is selected from the group consisting of $C_1$–$C_3$ alkyl, $C_1$–$C_2$ alkylamino, $C_2$–$C_4$ dialkylamino, and $C_2$–$C_4$ alkylalkoxyamino.

2. The compound of claim 1 wherein R is methyl, $R^1$ is methyl and $R^2$ is methylamino.

3. The compound of claim 1 wherein R is methyl, $R^1$ is methyl and $R^2$ is ethyl.

4. The compound of claim 1 wherein R is methyl, $R^1$ is methyl and $R^2$ in dimethylamino.

5. The compound of claim 1 wherein R is hydrogen, $R^1$ is methyl and $R^2$ is ethyl.

6. The compound of claim 1 wherein R is hydrogen, $R^1$ is methyl and $R^2$ is methylamino.

7. A herbicidal composition comprising an herbicidally effective amount of a compound having the structural formula

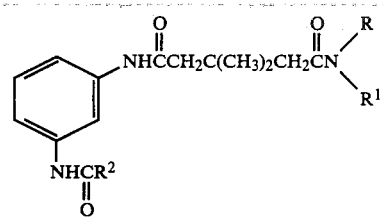

wherein R is selected from the group consisting of hydrogen or $C_1$–$C_3$ alkyl; $R^1$ is selected from the group consisting of $C_1$–$C_3$ alkyl; and $R^2$ is selected from the group consisting of $C_1$–$C_3$ alkyl, $C_1$–$C_2$ alkylamino, $C_2$–$C_4$ dialkylamino and $C_2$–$C_4$ alkylalkoxyamino; and an inert carrier.

8. The method of controlling undesirable vegetation comprising applying to the area where control is applying to the area where control is desired, an herbicidally effective amount of a compound having the formula

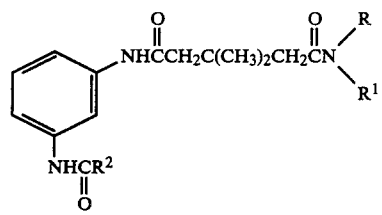

wherein R is selected from the group consisting of hydrogen or $C_1$–$C_3$ alkyl; $R^1$ is selected from the group consisting of $C_1$–$C_3$ alkyl; and $R^2$ is selected from the group consisting of $C_1$–$C_3$ alkyl, $C_1$–$C_2$ alkylamino, $C_2$–$C_4$ dialkylamino and $C_2$–$C_4$ alkylalkoxyamino.

9. The method of claim 8 wherein R is methyl, $R^1$ is methyl and $R^2$ is methylamino.

10. The method of claim 8 wherein R is methyl, $R^1$ is methyl and $R^2$ is ethyl.

11. The method of claim 8 wherein R is methyl, $R^1$ is methyl and $R^2$ in dimethylamino.

12. The method of claim 8 wherein R is hydrogen, $R^1$ is methyl and $R^2$ is ethyl.

13. The method of claim 8 wherein R is hydrogen, $R^1$ is methyl and $R^2$ is methylamino.

* * * * *